United States Patent [19]

Mross et al.

[11] 4,212,772

[45] Jul. 15, 1980

[54] CATALYST FOR THE MANUFACTURE OF ETHYLENE OXIDE

[75] Inventors: Wolf D. Mross; Eckart Titzenthaler, both of Ludwigshafen; Matthias Schwarzmann, Limburgerhof; Juergen Koopmann, Neustadt, all of Fed. Rep. of Germany

[73] Assignee: BASF Aktiengesellschaft, Fed. Rep. of Germany

[21] Appl. No.: 31,039

[22] Filed: Apr. 18, 1979

Related U.S. Application Data

[63] Continuation of Ser. No. 796,062, May 12, 1977, abandoned.

[30] Foreign Application Priority Data

May 19, 1976 [DE] Fed. Rep. of Germany ....... 2622228
Sep. 9, 1976 [DE] Fed. Rep. of Germany ....... 2640540
Sep. 11, 1976 [DE] Fed. Rep. of Germany ....... 2641000
Feb. 2, 1977 [DE] Fed. Rep. of Germany ....... 2704197

[51] Int. Cl.$^2$ .................. B01J 23/04; B01J 23/50
[52] U.S. Cl. ........................... 252/476; 260/348.34
[58] Field of Search ..................... 252/463, 476; 260/348.34

[56] References Cited

U.S. PATENT DOCUMENTS

| | | | |
|---|---|---|---|
| 2,404,438 | 7/1946 | Evans | 252/476 X |
| 2,615,900 | 10/1952 | Sears | 252/476 X |
| 3,563,913 | 2/1971 | Krijger et al. | 252/463 |
| 4,007,135 | 2/1977 | Hayden et al. | 252/476 X |
| 4,010,115 | 3/1977 | Nielsen et al. | 252/476 X |

*Primary Examiner*—W. J. Shine
*Attorney, Agent, or Firm*—Keil & Witherspoon

[57] ABSTRACT

A novel catalyst for the manufacture of ethylene oxide from ethylene by means of oxygen or air, comprising from 2 to 12% of silver on a conventional carrier, together with from 0.1 to 2 atom% (based on silver) of lithium and from 0.05 to 0.35 atom% of potassium or 0.003 to 0.25 atom% of rubidium or 0.0005 to 0.2 atom% of cesium or mixtures of potassium, rubidium and/or cesium in amounts exhibiting corresponding catalytic activity. The catalyst is advantageously obtained by heating a carrier which is impregnated with a silver complex compound.

7 Claims, No Drawings

CATALYST FOR THE MANUFACTURE OF ETHYLENE OXIDE

This is a continuation, of application Ser. No. 796,062, filed May 12, 1977, now abandoned.

The present invention relates to an improved catalyst for the manufacture of ethylene oxide, which comprises finely divided silver on a porous carrier, together with lithium and also potassium, rubidium and/or cesium (hereinafter referred to, for brevity, as heavy alkali metal) as promoters, the silver having been applied to the carrier in the form of a silver compound and having been converted to the active form by heating or by treatment with a reducing agent.

It has been disclosed that ethylene oxide can be obtained by the direct addition of elementary oxygen to ethylene in the gas phase in the presence of a silver catalyst. From considerations of the reaction mechanism, it is often assumed that the reaction can at most give a yield (selectivity) of about 85 mole%, based on ethylene converted, since part of the ethylene is always combusted to give carbon dioxide.

In practice, selectivities of from about 70 to 75% are achieved with the best known catalysts, but to meet the requirements of large commercial plants other characteristics are also critical, such as the largest possible conversion per unit space and unit time (space-time yields) and catalyst life. It is immaterial in this context that on an experimental scale, and at low oxygen conversion, higher yields are feasible.

A large number of processes for the manufacture of suitable silver catalysts have been disclosed. Normally, a coarse-pored chemically inert catalyst carrier is used and silver is deposited thereon in as finely a divided form as possible, e.g. by thermal decomposition of a silver salt of an organic carboxylic acid or of a silver complex compound (German Published Application DAS 1,211,607 and German Laid-Open Application DOS 2,159,346). Modifiers (promoters) are also added. The relevant proposals for improvement therefore relate to the carrier used, the addition of promoters and the process of manufacture of the catalyst (R. Landau and R. E. Lidov in "Ethylene and its Industrial Derivatives", published by S. A. Miller, Ernest Benn, London (1969), page 513, and D. J. Hucknall, "Selective Oxidations of Hydrocarbons", Academic Press, London (1974), page 6).

Additives (promoters) recommended for the silver catalysts are above all compounds of the alkaline earth metals, earth metals and rare earth metals (U.S. Pat. No. 2,238,474, German Published Application DAS No. 1,279,669 and German Laid-Open Application DOS No. 2,263,543). Recently, German Laid-Open Application DOS No. 2,300,512 has disclosed that compounds of the heavy alkali metals are superior to all previously known promoters. Sodium is stated to be distinctly inferior, as a promoter, to the heavy alkali metals (German Laid-Open Application DOS No. 2,448,449).

We have found that on modifying silver catalysts by using, as promoters, a specific combination of alkali metals, catalysts for the oxidation of ethylene may be produced which are superior to the conventional catalysts containing, for example, promoters chosen from the heavy alkali metals or the alkaline earth metals, as regards life, activity and selectivity. Furthermore, we have found, surprisingly, that if the reaction is carried out over the catalysts according to the invention, the oxygen conversion and gas hourly space velocity can be increased without accelerating the fall-off in catalytic activity. Particularly favorable results are obtained if a specific process is used to manufacture the catalyst.

The invention thus relates to a novel catalyst for the manufacture of ethylene oxide by reacting ethylene with oxygen, based on silver and alkali metals, or their compounds, applied to a carrier, in which catalyst are contained, based on the silver present, from 0.1 to 2 atom% of sodium and/or lithium and either from 0.05 to 0.35 atom% of potassium, 0.003 to 0.25 atom% of rubidium or 0.0005 to 0.2 atom% of cesium or a mixture of the heavy alkali metals (i.e. potassium, rubidium and cesium) in amounts exhibiting corresponding catalytic activity.

The catalyst may be obtained by applying a thermally decomposable silver compound and appropriate alkali metal compounds to the carrier, in any sequence, and activating the catalyst by heating and/or by means of reducing agents. In the former case, the temperature should in general not exceed 400° C. and preferably should not exceed 300° C. The minimum temperature is in general from 80° to 150° C.

The addition of sodium and/or lithium and heavy alkali metals, in amounts according to the invention, may be effected before applying the silver to the carrier or together with the application of the silver or following the latter, or even in a subsequent treatment of a finished or used silver catalyst.

The optimum amount of sodium to be used, according to the invention, in the silver catalyst, depends on the magnitude of the surface area of the carrier, the amount of silver and, to a lesser extent, the method of manufacture. The latter above all influences the limits of the sodium concentration range within which good catalysts are obtainable. The optimum amount of sodium and/or lithium can be most easily determined by a number of preliminary experiments, in which catalysts with varying amounts of sodium are manufactured in accordance with a specific method of manufacture, and their activity is examined.

In the case of the preferentially used coarse-pored carriers having a surface area of from 0.1 to 0.5 m$^2$/g it is advisable to use an amount of sodium and/or lithium of from 0.4 to 1.5 atom% (based on silver), assuming that the amount of silver is itself from 1 to 12%, especially from 5 to 10%, based on the weight of the catalyst, and the mean particle size of the silver is from 0.2 to 0.4 μm. Sodium and lithium appear to the substantially equivalent with respect to their specific influence on catalyst activity, life and selectivity. Mixtures of sodium and lithium in all proportions also appear to have a favorable influence.

As regards the promoters selected from the group of the heavy alkali metals, the amounts used in the catalysts according to the invention are, based on silver, either from 0.05 to 0.35 atom% of potassium or from 0.003 to 0.25 atom% of rubidium or from 0.0005 to 0.2 atom% of cesium or amounts of a mixture exhibiting corresponding catalytic activity. The optimum amount of heavy alkali metal depends on the amount of sodium. If a high sodium (lithium) content is chosen, the suitable content of heavy alkali metal lies in the lower part of the stated concentration ranges. To achieve a long catalyst life, it is advantageous to choose the highest possible sodium (lithium) content and the lowest possible heavy alkali metal content. Advantageous results are obtained with a heavy alkali metal content of from 0.05 to 0.2 atom% of potassium, from 0.03 to 0.2 atom% of rubidium or from 0.005 to 0.1 atom% of cesium.

It is to be assumed that in the finished catalyst the alkali metals are in the form of compounds. A suitable method of determination of the amount of alkali metal has proved to be treating the catalysts with dilute (10% strength) nitric acid and carrying out measurements on the resulting solution by conventional processes.

In principle, all methods proposed in the literature for the manufacture of silver catalysts may be used to manufacture the catalysts according to the invention (R. Landau and R. E. Lidov, loc. cit. and D. J. Hucknall, loc. cit.). The preferred method is to impregnate a coarse-pored carrier with the solution of a thermally decomposable silver salt, e.g. silver nitrate (U.S. Pat. No. 3,575,888) or silver lactate (German Published Application DAS No. 1,211,607) or of a silver complex compound, e.g. a silver amine-carboxylate complex (German Laid-Open Application DOS No. 2,159,346) and then to decompose the silver compound by treatment with a reducing agent and/or by heating.

Sodium (lithium) may be added to the impregnating solution, in the form of a sodium (lithium) compound. However, it is also possible to apply sodium (lithium) in the form of a sodium (lithium) compound to the carrier in a preliminary step, as described in principle in German Laid-Open Application DOS No. 2,448,449, and to treat the dried carrier with the silver formulation in a further step.

The heavy alkali metal or metals may, like the sodium, be added in the form of a solution of a compound. However, it is also possible to apply the heavy alkali metal to the carrier in a preliminary step or to impregnate the otherwise finished catalyst with the solution of a compound of the heavy alkali metal, e.g. in an organic solvent. The promoters can of course also be applied simultaneously by adding a solution which contains both sodium (lithium) and heavy alkali metal, as well as silver. In some cases it may be advantageous to subsequently impregnate a catalyst, which already contains sodium (lithium) and silver, with a solution of a heavy alkali metal compound in a solvent (which may or may not be an organic solvent), as described in German Published Application DAS No. 2,519,599.

In a particularly preferred method of manufacture, the carrier is impregnated with an aqueous solution of a thermally decomposable silver complex compound, a sodium (lithium) compound and a compound of a heavy alkali metal, is then preferably treated with water vapor, with or without heating and/or with exposure to reducing gases, until the silver compound begins to decompose, i.e. until there is a distinct discoloration, and is thereafter brought to the catalytically active form by heating to constant weight at from 150° to 300° C.

Suitable silver complex compounds are silver salts which contain co-ordinatively bound ligands. Suitable complex-forming agents are, in particular, amines which form readily water-soluble silver complex salts and the salts of which decompose easily, the undesired decomposition products being readily volatile. Other complex-forming agents are polybasic carboxylic acids, e.g. oxalic acid.

Examples of amines are primary amines in which alkyl is substituted or unsubstituted and of 1 to 8 carbon atoms (e.g. n-butylamine or ethanolamine), polyamines of the alkanes up to about hexane (e.g. ethylenediamine, diethylenetriamine or hexamethylenediamine), monoalicyclic amines, e.g. cyclohexylamine, and monoheterocyclic amines, e.g. pyrrolidine, piperidine and morpholine. Ammonia may also be used, but industrially its use is less advisable because explosive silver-nitrogen compounds are readily formed.

The anion of the silver complex can substantially be chosen as desired; all that is necessary is that the anion or its decomposition products should be volatile on heating. For example, virtually all carboxylates, as well as the carbonate, isocyanate, cyanide, nitrite and nitrate may be used.

Amine complexes of silver nitrate are preferred because silver nitrate is the cheapest silver chemical and also the silver chemical obtainable in the purest form. To form the complex, it is advantageous to add to the impregnating solution the amount of amine required for the stoichiometric formation of the complex of the formula:

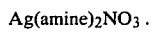

$$Ag(amine)_2NO_3.$$

In this formula, each "amine" is an amino group or an equivalent ligand. According to the invention, amines of the general formula

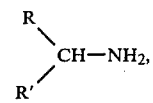

where R and R' are aliphatic radicals, or diamines of the general formula $H_2N$—A—$NH_2$, wherein —A— is a divalent aliphatic or cycloaliphatic hydrocarbon radical, are preferred.

The anion of the sodium (lithium) compound and of the heavy alkali metal compound can also substantially be chosen as desired. It is advantageous to use sodium (lithium) compounds and heavy alkali metal compounds which are readily water-soluble and the anions of which, when mixed with a solution containing silver ions, do not cause the latter to precipitate. Compounds of which the anions contain catalyst poisons such as halogens and chalcogens, which can only be removed again with difficulty, are less suitable.

In the preferred method of manufacture, the first treatment step comprises the impregnation with a solution or suspension of a silver compound and the promoter solutions, after which a certain proportion (possibly only a fraction) of the silver compound is decomposed to silver under conditions such that there is virtually no loss of moisture, i.e. in an atmosphere which is more or less saturated with water vapor. This can be done by heating the impregnated carrier in a heated cabinet or oven in an atmosphere which is more or less saturated with water vapor.

In place of, or additionally to heating the material, treatment with a reducing gas (CO or $H_2$) saturated with water vapor may be carried out.

When using a silver amine complex compound, the end of the first treatment step can be recognized from the fact that the initially colorless or white catalyst precursor, i.e. the impregnated moldings, assumes a gray to dark gray discoloration. The treatment is complete when no further discoloration takes place. Excessively long treatment must be avoided. It is advantageous to determine the optimum duration of treatment by a preliminary experiment in which the maximum catalytic activity is determined as a function of this duration of treatment.

E.g., at 90° C. in an atmosphere saturated with water vapor, the optimum treatment time of a carrier impregnated with a silver isopropylamine nitrate complex salt is one hour. The same result is achieved by 20 minutes' treatment of the impregnated carrier with carbon monoxide (saturated with water vapor) at room temperature.

In a further step, the catalyst precursor obtained is heated, preferably in an atmosphere containing $CO_2$, within a brief period, preferably within 10 minutes, to a temperature at which, for example when using a silver amine nitrate complex, a strongly exothermic reaction commences. This temperature can readily be determined by a preliminary experiment, for example with the aid of differential thermo-analysis.

In the case of other complexes, for example with oxalic acid, an endothermic reaction occurs in this step.

In the case of the above silver isopropylamine nitrate complex, the temperature at which a strongly exothermic reaction commences is about 180° C. As soon as this temperature has been reached, good heat exchange with the environment must be ensured to avoid an excessive autogenous temperature rise of the catalyst; the catalyst temperature should in such cases not exceed 300° C.

The catalysts of the invention in general contain from 2 to 12%, especially from 5 to 10%, of silver, based on the weight of the carrier. Although larger amounts of silver (e.g. up to 20%) do not impair the activity of the catalyst, industrially such larger amounts serve no purpose.

The carrier will generally consist of a heat-resistant chemically inert material, e.g. α-alumina, silicon carbide, graphite or highly sintered aluminum silicate. The content of uncontrolled impurities which can be dissolved out by boiling with dilute nitric acid will generally not exceed 0.001% by weight of alkali metal ions and 0.03% by weight of alkaline earth metal ions and earth metal ions. Of course, purification of the carrier may in certain cases be dispensed with if the carrier contains, for example, sodium, the amount of which is taken into account in the calculation, and if other constituents, which might interfere, are not present.

The porosity of the carrier will generally be as high as possible (preferably greater than 40% by volume) and the nature of the pores will generally be such that the degree of pore utilization is virtually 1, i.e. the carrier should, if possible, only possess pores of a diameter greater than 1,000 nm, which are readily accessible to gas molecules by diffusion. Suitable carriers are commercially available.

The silver catalysts according to the invention which contain sodium (lithium) or sodium (lithium) compounds and heavy alkali metal or heavy alkali metal compounds may be used for all processes in which ethylene oxide is manufactured by direct oxidation of ethylene with molecular oxygen. A review of such processes is to be found in a series of articles in Hydrocarbon Processing (March 1976, 69-72, 73-77, 78-80). For example, the catalysts of the invention may be used both in air oxidation processes and in oxygen oxidation processes. Optimum selectivities are only obtained—as is also the case with other industrially used ethylene oxide catalysts—if an inhibitor, e.g. a chlorinated polyphenyl compound, 1,2-dichloroethane or vinyl chloride, is present to control the catalytic action.

The catalysts according to the invention are superior to the catalysts of the prior art in respect of activity and selectivity when used in processes in which the synthesis gas contains approximately equal percentages, e.g. from 4 to 8%, of ethylene and oxygen (in addition to diluents, e.g. nitrogen, carbon dioxide and argon; see Use Example 1).

In processes which use a substantial excess of ethylene over oxygen (e.g. 25 to 35% ethylene; 4 to 10% oxygen; rest: methane, argon, carbon dioxide in the synthesis gas, the superiority of the novel catalysts over the catalysts of the prior art is particularly significant in respect of activity and life.

In both types of process, the reaction temperature is between 200° and 300° C., the lower temperatures of, say, 200° to 250° C. being generally used at lower gas velocities and in lower oxygen conversion-type processes, and the higher temperatures of, say, 230° to 280° C. being those conventionally used in processes which employ a synthesis gas which reacts relatively slowly, e.g. air oxidation processes.

The gas hourly space velocities may be between 1,500 and 5,000 ($m^3$ per $m^3$ and hour under S.T.P. conditions) or even higher. The pressures are generally above atmospheric and may be between 10 and 30 bars in the case of commercial-scale processes.

The superiority of the novel catalysts manifests itself particularly clearly if the comparison is carried out at high throughputs over the catalyst (high oxygen conversions of ~50 percent and/or high gas hourly space velocities of 4,000

$$\frac{\text{liters (S.T.P.) of gas}}{\text{liter of catalyst} \times \text{hr}}$$

(Use Example 3).

EXAMPLE 1

14.2 g of silver nitrate are dissolved in 100 ml of water and an equimolar amount of a 5 percent strength sodium hydroxide solution is added at room temperature, while stirring. The resulting silver oxide precipitate is washed eight times with water and the wash water is centrifuged off. 2 ml of an 0.2-normal NaOH solution and 0.5 ml of a 0.1-normal CsOH solution are added to the moist precipitate and this material is applied, by tumbling, to 100 g of a spherical α-alumina (mullite) carrier (type SA 5252 manufactured by NORTON, Acron, Ohio, U.S.A.). During the tumbling process, the material is heated, and dried, by means of an infrared lamp. The catalyst precursor obtained is then further dried at 105° C., after which it is heated in air at 380° C. This catalyst is designated A (Table 1).

EXAMPLE 2

Silver oxide is prepared as in Example 1 and the moist precipitate is dissolved in 8.9 g of 85% strength lactic acid by heating. 2.5 ml of a 2.15 percent strength $NaNO_3$ solution and 1.5 ml of a 1 percent strength cesium nitrate solution are added and the combined solution is made up with water to a volume corresponding to the water absorption of 100 g of carrier pellets (type 5151 manufactured by NORTON). The solution is allowed to act on the carrier for one hour at 90° C. The impregnated carrier is then kept under carbon monoxide for 20 minutes, after which it is placed in a through-circulation dryer. It is kept for 30 minutes at 250° C. and then for 30 minutes at 380° C. The catalyst obtained is designated B (Table 1).

EXAMPLE 3

13.9 g of silver nitrate are dissolved in 6 ml of water and 9.7 g of isopropylamine are added whilst cooling. 3.8 ml of an aqueous 2.15 percent strength sodium nitrate solution and 0.2 ml of a 1 percent strength aqueous cesium nitrate solution are then added. The mixture is made up with water to a volume corresponding to the expected liquid absorption of the carrier as found in a preliminary experiment. 100 g of carrier (NORTON SA 5551) are impregnated under reduced pressure and the impregnated carrier (catalyst precursor) is kept at 90° C. for one hour in a through circulation dryer which also contains an open dish of water. The catalyst precursor treated in this way is taken out and heated to 240° C., and the water vapor atmosphere is replaced by an atmosphere of $CO_2$ or $N_2$. The catalyst precursor is then returned to the dryer and the evolution of gas is allowed to subside, after which the catalyst is cooled. It is designated C 1 (Table 1).

EXAMPLE 4

The following series of experiments is suited to show the dependence of catalyst properties on alkali metal content:

The catalyst is prepared as in Example 3, but the amount of added sodium nitrate and cesium nitrate solutions is varied (for the contents of silver, and of sodium and cesium which are soluble in dilute nitric acid, in Catalysts C 2 to C 7, see Table 1).

EXAMPLE 5

The catalyst is prepared as in Example 1, but instead of the cesium nitrate solution, a corresponding amount of rubidium nitrate solution is added (Catalyst D, Table 1).

EXAMPLE 6

The catalyst is prepared as in Example 3, but instead of the cesium nitrate solution, a corresponding amount of potassium nitrate solution is added (Catalyst E, Table 1).

EXAMPLE 7

3.6 ml of an aqueous 2.15 percent strength sodium nitrate solution are made up with water to a volume corresponding to the liquid absorption of the carrier. 100 g of the carrier are impregnated with this solution under reduced pressure. The impregnated carrier is then dried for 30 minutes at 250° C. The silver and cesium are applied as in Example 3 (Catalyst F, Table 1).

EXAMPLE 8

A catalyst corresponding to that of Comparative Experiment 4, given below, is first prepared; 100 g portions thereof are impregnated with 20 ml of a solution of 150 ppm of cesium carbonate in methanol, and are then dried for 10 minutes at 250° C. (Catalyst G, Table 1).

EXAMPLE 9

A sample of the Catalyst P obtained in the Comparative Experiment 4 described below is exposed to operating conditions for one month in a test reactor, as described in Use Example 1; it is then treated, in the reactor, with a solution of $CsNO_3$ in methanol, which contains 0.5 percent of $H_2O$. The test reactor is then heated to 130° C. and at the same time flushed with nitrogen. The catalyst obtained is designated H (Table 1).

EXAMPLES 10 to 14

The catalyst is prepared as in Example 3 or 4; to show the action of exceptionally small amounts of promoters, the amount of added sodium nitrate solution and cesium nitrate solution is varied as shown in Table 2 below.

EXAMPLES 15 to 17

The catalyst is prepared as in Example 3 or 5; instead of cesium nitrate solution, exceptionally small amounts of rubidium nitrate solution are employed (see Table 2).

EXAMPLE 18

13.9 g of silver nitrate are dissolved in 12 g of sec-butylamine. 0.3 ml of an 8 percent strength aqueous $CsNO_3$ solution and 0.25 ml of an aqueous $LiNO_3$ solution (obtained by placing 22.75 g of $LiNO_3$ in a flask and filling the flask with water up to the 100 ml mark) are added to this solution. The combined solution is made up with water to a volume corresponding to the expected liquid absorption of the carrier as found in a preliminary experiment. 100 g of carrier (type SA 5551 manufactured by NORTON) are impregnated under reduced pressure and stored for 1 day at room temperature. The impregnated catalyst is then placed in a through-circulation dryer which has been preheated to 240° C. and has a $CO_2$ or $N_2$ atmosphere. After gas evolution is over, the catalyst is removed from the dryer. The catalyst obtained is designated L 1 (Tables 5a and 5b).

EXAMPLE 19

The catalyst is prepared as in Example 18 except that the $CsNO_3$ and $LiNO_3$ solutions are replaced by 0.1 ml of 8 percent strength $CsNO_3$ solution, 0.25 ml of $LiNO_3$ solution as described in Example 18 and 0.15 ml of $NaNO_3$ solution (obtained by placing 25.8 g of $NaNO_3$ in a flask and filling the flask with water up to the 100 ml mark).

The catalyst obtained is designated L 2 (Tables 5a and 5b).

The improvements achieved by the invention are shown particularly clearly by comparison with the conventional catalysts described below:

COMPARATIVE EXPERIMENT 1

41.4 g of silver nitrate are dissolved in 220 ml of water. An equimolecular amount of a 5 percent strength aqueous sodium hydroxide solution is added at from 15° to 20° C., while stirring. The precipitate is washed eight times with water and the wash water is separated off. 2.1 g of barium and 0.033 g of aluminum, each as the lactate and each dissolved in 7 ml of water, are added to the moist precipitate with vigorous stirring. In a rotating drum, 150 kg of carrier in spherical form (NORTON type SA 5252) are heated at 60°–70° C. by infrared heating and sprayed with the silver oxide suspension. The catalyst is dried at 105° C. and is kept in air at 380° C. for one hour. It is analyzed by treatment with 10 percent strength hot nitric acid in a platinum dish. The solution is found to contain 11.8 percent of silver, 0.91 percent of barium and 0.03 percent of aluminum, based on the finished catalyst. The catalyst is designated M.

COMPARATIVE EXPERIMENT 2

The silver oxide is prepared as described above; however, the moist precipitate is merely stirred with 8.9 g of an 85 percent strength aqueous lactic acid solution at room temperature. 100 g of carrier (NORTON type 5151) are introduced into the resulting silver lactate solution. The solution is then concentrated at room temperature, under a pressure of about 40 millibars, whilst being stirred slowly, until it has been almost completely absorbed by the carrier. The resulting catalyst precursor is heated in a cabinet dryer for 2 hours at 250° C. and 30 minutes at 380° C. The finished catalyst contains 7.8 percent of silver (Catalyst N).

COMPARATIVE EXPERIMENT 3

12.4 g of freshly precipitated silver oxalate which has been washed free from alkali are dissolved, whilst cooling, in an aqueous solution of 4.92 g of ethylenediamine and 2.0 g of ethanolamine. 1.6 ml of a 1 percent strength aqueous $CsNO_3$ solution are added and the mixture is made up with water to a volume corresponding to the liquid absorption of the carrier. 100 g of carrier (NORTON SA 5551) are impregnated with the solution under reduced pressure. The carrier is immediately placed in a through-circulation dryer at 290° C. The total period of heating is 3 hours (Catalyst O).

COMPARATIVE EXPERIMENT 4

The procedure described in Example 3 is followed, except that the $CsNO_3$ is not added. The catalyst is designated P.

COMPARATIVE EXPERIMENT 5

The procedure of Example 4 is followed, but the amount of cesium nitrate added is 10 times that for Catalyst C6. Catalyst R.

USE EXAMPLE 1

The Catalysts A and H obtained according to Examples 1 to 9 and M to R are comminuted and 10 g portions of the 0.6–0.75 mm sieve fraction are filled into a glass reactor of 5 mm internal diameter. The reactor is introduced into a metal bath, the temperature of which is regulated. A gas composed of 7% of ethylene, 9.7% of oxygen and 0.3 ppm of inhibitor, the remainder being nitrogen, is passed over the catalyst under atmospheric pressure. The gas hourly space velocity is 2,000

$$\frac{\text{liters (S.T.P.) of gas}}{\text{liter of catalyst} \times \text{hr}}.$$

The temperature is regulated to give an oxygen conversion of 40%. After about 60 hours, the temperature has stabilized and after 90 hours samples are taken and the selectivity is determined. The results are summarized in Tables 1 and 5a.

USE EXAMPLE 2

Some of the above catalysts are comminuted and 10 g portions of the 0.6–0.75 mm sieve fraction are introduced into a stainless steel reactor of 5 mm internal diameter. The reactor has a jacket through which a thermostated fluid is passed. A gas composed of 30% of ethylene, 8% of oxygen and 3 ppm of inhibitor, the remainder being nitrogen, is passed through the reactor. The pressure is 16 bars and the gas hourly space velocity is 3,300

$$\frac{\text{liters (S.T.P.) of gas}}{\text{liter of catalyst} \times \text{hr}}.$$

The temperature is regulated to give an oxygen conversion of 50%. After 2 days, samples are taken and the activity and selectivity are determined (Tables 2, 3 and 5b).

USE EXAMPLE 3

Catalysts C1, C4, F, O and P, in a non-comminuted form, are introduced in amounts of 10 kg into a pressure-resistant tubular steel reactor which corresponds to a single tube conventionally used in industrial plants. The reactor has a jacket through which a thermostated fluid is passed. A gas of the approximate composition 30% of ethylene, 8% of oxygen, 6.5 percent of $CO_2$, 4 percent of argon, 3 ppm of inhibitor and 50 percent of methane is passed through the reactor. The pressure is 16 bars. The temperature of the cooling medium of the reactor is so adjusted, in a first series of Experiments a, that at a gas hourly space velocity of 2,000

$$\frac{\text{cubic meters (S.T.P.) of gas}}{\text{cubic meter of catalyst} \times \text{hr}},$$

an oxygen conversion of 35 percent is reached. In a second series of experiments, 50% of the oxygen is converted at a gas hourly space velocity of 4,000

$$\frac{\text{cubic meters (S.T.P.) of gas}}{\text{cubic meter of catalyst} \times \text{hr}}.$$

Samples are, in each case, taken after one week and after 3 months (Tables 4a and 4b).

USE EXAMPLE 4

The catalysts obtained according to Examples 18 and 19 are tested as described in Use Example 1 and Use Example 2 respectively. The results are given in Tables 5a and 5b.

TABLE 1

| Catalyst | Silver content (% by weight) | Alkali metal content in the acid-soluble material (atom %, based on silver) | | | Temperature (°C.) for 40% conversion in a short-term experiment | Selectivity (%) |
|---|---|---|---|---|---|---|
| A  | 7.8  | 0.08 ($Cs^+$) | 0.84 ($Na^+$) | 0.03 ($K^+$)[x] | 288 | 70.5 |
| B  | 7.9  | 0.09 ($Cs^+$) | 0.65 ($Na^+$) | 0.04 ($K^+$) | 267 | 73.5 |
| C1 | 7.7  | 0.01 ($Cs^+$) | 1.25 ($Na^+$) | 0.02 ($K^+$) | 252 | 78.5 |
| C2 | 7.7  | 0.10 ($Cs^+$) | 0.13 ($Na^+$) | 0.03 ($K^+$) | 254 | 78.0 |
| C3 | 7.85 | 0.08 ($Cs^+$) | 0.37 ($Na^+$) | 0.04 ($K^+$) | 249 | 77.5 |
| C4 | 7.75 | 0.06 ($Cs^+$) | 0.75 ($Na^+$) | 0.02 ($K^+$) | 253 | 78.5 |
| C5 | 7.95 | 0.03 ($Cs^+$) | 1.11 ($Na^+$) | 0.04 ($K^+$) | 257 | 78.5 |
| C6 | 7.8  | 0.01 ($Cs^+$) | 1.53 ($Na^+$) | 0.03 ($K^+$) | 261 | 78.5 |
| C7 | 7.9  | 0.01 ($Cs^+$) | 2.04 ($Na^+$) | 0.03 ($K^+$) | 281 | 77.0 |
| D  | 7.75 | 0.08 ($Rb^+$) | 0.73 ($Na^+$) | 0.01 ($K^+$) | 251 | 77.5 |

TABLE 1-continued

| Catalyst | Silver content (% by weight) | Alkali metal content in the acid-soluble material (atom %, based on silver) | | | Temperature (°C.) for 40% conversion in a short-term experiment | Selectivity (%) |
|---|---|---|---|---|---|---|
| E | 7.0 |  | 0.74 (Na+) | 0.10 (K+)$^{xx}$ | 259 | 77.0 |
| F | 7.8 | 0.03 (Cs+) | 1.15 (Na+) | 0.03 (K+) | 251 | 78.0 |
| G | 7.9 | 0.02 (Cs+) | 1.27 (Na+) | 0.02 (K+) | 253 | 78.0 |
| H | 7.9 | 0.02 (Cs+) | 1.25 (Na+) | 0.02 (K+) | 252 | 78.5 |
| M | 11.8 |  | 0.07 (Na+)$^x$ | 0.03 (K+) | 287 | 67.5 |
| N | 7.8 |  | 0.09 (Na+)$^x$ | 0.01 (K+) | 273 | 70.0 |
| O | 7.9 | 0.10 (Cs+) | 0.09 (Na+)$^x$ | 0.03 (K+) | 264 | 75.5 |
| P | 7.8 |  | 1.26 (Na+) | 0.02 (K+) | 261 | 76.0 |
| R | 7.8 | 0.10 (Cs+) | 1.53 (Na+) | 0.03 (K+) | 291 | 73.5 |

$^x$All potassium contents, except in the case of E, are impurities, considered to be permissible, in amounts below the range according to the invention.
$^{xx}$The appropriate amount of potassium was added.

TABLE 2

| Example | Alkali metal content in the acid soluble material (atom %, based on silver) | | | Temperature (°C.) for 50% conversion of $O_2$ | Selectivity % |
|---|---|---|---|---|---|
| 10 | 0.001 (Cs+) | 1.65 (Na+) | 0.02 (K+)$^x$ | 217 | 76.5 |
| 11 | 0.005 (Cs+) | 1.68 (Na+) | 0.03 (K+)$^x$ | 219 | 78.0 |
| 12 | 0.0075 (Cs+) | 1.67 (Na+) | 0.02 (K+)$^x$ | 218 | 79.5 |
| 13 | 0.01 (Cs+) | 1.62 (Na+) | 0.04 (C+)$^x$ | 218 | 80.5 |
| 14 | 0.005 (Cs+) | 0.92 (Na+) | 0.03 (K+)$^x$ | 217 | 78.5 |
| 15 | 0.003 (Rb+) | 1.69 (Na+) | 0.04 (K+)$^x$ | 219 | 75.5 |
| 16 | 0.008 (Rb+) | 1.72 (Na+) | 0.02 (K+)$^x$ | 220 | 77.0 |
| 17 | 0.03 (Rb+) | 1.65 (Na+) | 0.03 (K+)$^x$ | 217 | 77.5 |

$^x$All potassium contents are present in the form of impurities in the starting materials and are below the amounts according to the invention.

TABLE 3

| Catalyst | Temperature (°C.) for 50% $O_2$ conversion in a short-term experiment | Selectivity (%) |
|---|---|---|
| C1 | 220 | 80.5 |
| C2 | 219 | 79.5 |
| C4 | 220 | 80.5 |
| C7 | 231 | 79.0 |
| D | 218 | 78.0 |
| E | 234 | 77.5 |
| O | 233 | 78.5 |
| P | 234 | 75.5 |

TABLE 4a

| Catalyst | Temperature (°C.) for 35% $O_2$ conversion | Selectivity (%) |
|---|---|---|
| (a1) after 1 week | | |
| C1 | 205 | 81.5 |
| C4 | 203 | 81.5 |
| F | 204 | 81.0 |
| O | 224 | 80.5 |
| P | 203 | 76.5 |
| (a2) after 3 months | | |
| C1 | 205 | 81.5 |
| C4 | 203 | 81.5 |
| F | 204 | 81.0 |
| O | 231 | 77.5 |
| P | 203 | 76.5 |

TABLE 4b

| Catalyst | Temperature (°C.) for 50% $O_2$ conversion | Selectivity (%) |
|---|---|---|
| (b1) after 1 week | | |
| C1 | 234 | 79.5 |
| C4 | 236 | 79.0 |
| F | 234 | 79.5 |
| O | 251 | 78.0 |
| P | 231 | 75.5 |
| (b2) after 3 months | | |
| C1 | 234 | 79.5 |
| C4 | 235 | 78.5 |
| F | 234 | 79.5 |
| O | 266 | 74.5 |
| P | 231 | 75.5 |

TABLE 5a

| Catalyst | Silver content (% by weight) | Alkali metal content in the acid-soluble material (atom %, based on silver) | | | | Temperature (°C.) for 40% $O_2$ conversion | Selectivity (%) |
|---|---|---|---|---|---|---|---|
| L1 | 7.7 | 0.15 (Cs+) | 0.09 (Na+) | 0.03 (K+) | 1.0 (Li+) | 252 | 78.5 |
| L2 | 7.9 | 0.05 (Cs+) | 0.55 (Na+) | 0.02 (K+) | 1.0 (Li+) | 254 | 79.0 |

TABLE 5b

| Catalyst | Temperature (°C.) for 50% $O_2$ conversion | Selectivity (%) |
|---|---|---|
| L1 | 214 | 80.5 |
| L2 | 216 | 81.0 |

We claim:
1. A catalyst for the manufacture of ethylene oxide by reacting ethylene with oxygen, said catalyst comprising silver and alkali metal compounds on a carrier, in which catalyst are contained, based on the silver present, from 0.1 to 2 atom% of lithium and either from 0.05 to 0.35 atom% of potassium or from 0.003 to 0.25 atom% of rubidium or from 0.0005 to 0.2 atom% of cesium or a mixture of two or more of potassium, rubidium and cesium in amounts exhibiting corresponding catalytic activity.

2. A catalyst as set forth in claim 1, which has been obtained by applying a thermally decomposable silver compound and appropriate alkali metal compounds to the carrier, in any sequence, and activating the catalyst by heating at temperatures of from 80° to 400° C. and/or by means of a reducing agent.

3. A catalyst as set forth in claim 1, in which the proportion of silver is from 2 to 12%, based on the weight of the catalyst.

4. A catalyst as set forth in claim 1, which has been obtained by treating the carrier, impregnated with an aqueous solution of a silver complex salt compound and the alkali metal compounds, with water vapor until the silver complex salt has been decomposed, and then heating the product at from 80° to 400° C. until it reaches constant weight.

5. A catalyst as set forth in claim 3, wherein the mean particle size of the silver is from 0.2 to 0.4 $\mu$m, the surface area of the carrier is 0.1 to 0.5 $m^2/g$ and the amount of lithium used is from 0.4 to 1.5 atom%, based on silver.

6. A catalyst as set forth in claim 1, wherein from 0.05 to 0.2 atom% of potassium, from 0.03 to 0.2 atom% of rubidium or from 0.005 to 0.1 atom% of cesium is used.

7. A catalyst as set forth in claim 1, which has been obtained by treating the carrier, impregnated with an aqueous solution of a silver complex salt compound and the alkali metal compounds, with water vapor until the silver complex begins to decompose and heating the carrier at temperatures of from 150° to 300° C. until a constant weight is reached.

* * * * *